US008512378B2

(12) United States Patent
Green et al.

(10) Patent No.: US 8,512,378 B2
(45) Date of Patent: Aug. 20, 2013

(54) SUTURE ANCHOR

(75) Inventors: Michael L. Green, Pleasanton, CA (US); Bart Bojanowski, San Jose, CA (US); Joseph C. Tauro, Brick, NJ (US); John P. Greelis, Carlsbad, CA (US); Malcolm Heaven, Reno, NV (US)

(73) Assignee: KFx Medical Corporation, Carlsbad, CA (US)

( * ) Notice: Subject to any disclaimer, the term of this patent is extended or adjusted under 35 U.S.C. 154(b) by 0 days.

(21) Appl. No.: 13/302,299

(22) Filed: Nov. 22, 2011

(65) Prior Publication Data
US 2012/0065680 A1    Mar. 15, 2012

Related U.S. Application Data

(60) Division of application No. 11/557,027, filed on Nov. 6, 2006, now Pat. No. 8,062,334, which is a continuation-in-part of application No. 11/143,007, filed on Jun. 1, 2005, now Pat. No. 7,585,311.

(60) Provisional application No. 60/576,477, filed on Jun. 2, 2004, provisional application No. 60/610,924, filed on Sep. 17, 2004, provisional application No. 60/634,174, filed on Dec. 7, 2004, provisional application No. 60/753,445, filed on Dec. 22, 2005.

(51) Int. Cl.
*A61B 17/04* (2006.01)
(52) U.S. Cl.
USPC .......................................... 606/232; 411/38

(58) Field of Classification Search
USPC ........... 606/68, 198, 232, 313–314, 326–327, 606/300–301, 323, 272; 411/32–35, 38, 411/80.1–80.6, 913
See application file for complete search history.

(56) References Cited

U.S. PATENT DOCUMENTS

| 3,623,192 A | 5/1969 | Button |
| 4,210,148 A | 7/1980 | Stivala |
| 4,532,926 A | 8/1985 | O'Holla |
| 4,796,612 A | 1/1989 | Reese |

(Continued)

FOREIGN PATENT DOCUMENTS

| SU | 1600713 | 10/1990 |
| WO | WO 99/52478 A1 | 10/1999 |

(Continued)

OTHER PUBLICATIONS

Lo et al., Double-row arthroscopic rotator cuff repair: re-establishing the footprint of the rotator cuff, *Arthroscopy: The Journal of Arthroscopic and Related Surgery*, 19(9):1035-1042 (2003).

(Continued)

*Primary Examiner* — Gregory Anderson
(74) *Attorney, Agent, or Firm* — Knobbe, Martens, Olson & Bear LLP

(57) ABSTRACT

A bone anchor is described having pre-attached suture material. After insertion, lateral wings can be deployed on the bone anchor to prevent anchor pull-out. The suture may be attached at the tip of the anchor by tying it to a wire hook secured in a cavity in the anchor tip. The anchor may be inserted and deployed using an anchor inserter that is configured to apply an axial force to the anchor, thereby deforming the anchor to form the lateral wings.

15 Claims, 16 Drawing Sheets

(56) References Cited

U.S. PATENT DOCUMENTS

| | | | |
|---|---|---|---|
| 4,828,439 A * | 5/1989 | Giannuzzi | 411/37 |
| 4,898,156 A | 2/1990 | Gatturna et al. | |
| 4,946,468 A | 8/1990 | Li | |
| 5,013,316 A | 5/1991 | Goble et al. | |
| 5,074,050 A | 12/1991 | Williams | |
| 5,192,303 A | 3/1993 | Gatturna et al. | |
| 5,219,359 A | 6/1993 | McQuilkin et al. | |
| 5,224,946 A | 7/1993 | Hayhurst et al. | |
| 5,269,784 A | 12/1993 | Mast | |
| 5,336,240 A | 8/1994 | Metzler et al. | |
| 5,370,662 A | 12/1994 | Stone et al. | |
| 5,372,604 A | 12/1994 | Trott | |
| 5,417,712 A | 5/1995 | Whittaker et al. | |
| 5,423,858 A | 6/1995 | Bolanos et al. | |
| 5,423,860 A | 6/1995 | Lizardi et al. | |
| 5,443,482 A | 8/1995 | Stone et al. | |
| 5,472,452 A | 12/1995 | Trott | |
| 5,478,353 A | 12/1995 | Yoon | |
| 5,500,001 A | 3/1996 | Trott | |
| 5,527,341 A | 6/1996 | Gogolewski et al. | |
| 5,527,343 A | 6/1996 | Bonutti | |
| 5,543,012 A | 8/1996 | Watson et al. | |
| 5,545,180 A | 8/1996 | Le et al. | |
| 5,569,306 A | 10/1996 | Thal | |
| 5,575,801 A | 11/1996 | Habermeyer et al. | |
| 5,578,057 A | 11/1996 | Wenstrom, Jr. | |
| 5,584,835 A | 12/1996 | Greenfield | |
| 5,591,207 A | 1/1997 | Coleman | |
| 5,634,926 A | 6/1997 | Jobe | |
| 5,658,313 A | 8/1997 | Thal | |
| 5,665,112 A | 9/1997 | Thal | |
| 5,683,419 A | 11/1997 | Thal | |
| 5,690,676 A | 11/1997 | DiPoto et al. | |
| 5,697,950 A | 12/1997 | Fucci et al. | |
| 5,720,765 A | 2/1998 | Thal | |
| 5,725,557 A | 3/1998 | Gatturna et al. | |
| 5,769,894 A | 6/1998 | Ferragamo | |
| 5,800,436 A | 9/1998 | Lerch | |
| 5,814,072 A | 9/1998 | Bonutti | |
| 5,891,168 A | 4/1999 | Thal | |
| RE36,289 E | 8/1999 | Le et al. | |
| 5,948,001 A | 9/1999 | Larsen | |
| 5,948,002 A | 9/1999 | Bonutti | |
| 5,951,590 A | 9/1999 | Goldfarb | |
| 5,964,769 A | 10/1999 | Wagner et al. | |
| 5,964,783 A | 10/1999 | Grafton et al. | |
| 6,010,525 A | 1/2000 | Bonutti et al. | |
| 6,013,077 A | 1/2000 | Harwin | |
| 6,013,083 A | 1/2000 | Bennett | |
| 6,027,523 A | 2/2000 | Schmieding | |
| 6,045,573 A | 4/2000 | Wenstrom, Jr. et al. | |
| 6,045,574 A | 4/2000 | Thal | |
| 6,056,751 A | 5/2000 | Fenton, Jr. | |
| 6,063,106 A | 5/2000 | Gibson | |
| 6,093,201 A | 7/2000 | Cooper et al. | |
| 6,093,301 A | 7/2000 | Van Atta | |
| 6,099,547 A | 8/2000 | Gellman et al. | |
| 6,110,207 A | 8/2000 | Eichhorn et al. | |
| 6,117,160 A | 9/2000 | Bonutti | |
| 6,117,161 A | 9/2000 | Li et al. | |
| 6,126,677 A | 10/2000 | Ganaja et al. | |
| 6,149,669 A | 11/2000 | Li | |
| 6,200,330 B1 | 3/2001 | Benderev et al. | |
| 6,241,749 B1 | 6/2001 | Rayhanabad | |
| 6,245,082 B1 | 6/2001 | Gellman et al. | |
| 6,267,766 B1 | 7/2001 | Burkhart | |
| 6,280,474 B1 | 8/2001 | Cassidy et al. | |
| 6,293,961 B2 | 9/2001 | Schwartz et al. | |
| 6,296,659 B1 | 10/2001 | Foerster | |
| 6,306,159 B1 | 10/2001 | Schwartz et al. | |
| 6,319,271 B1 | 11/2001 | Schwartz et al. | |
| 6,328,758 B1 * | 12/2001 | Tornier et al. | 606/232 |
| 6,391,030 B1 | 5/2002 | Wagner et al. | |
| 6,423,065 B2 | 7/2002 | Ferree | |
| 6,432,123 B2 | 8/2002 | Schwartz et al. | |
| 6,464,713 B2 | 10/2002 | Bonutti | |
| 6,491,714 B1 | 12/2002 | Bennett | |
| 6,514,274 B1 | 2/2003 | Boucher et al. | |
| 6,518,200 B2 | 2/2003 | Lin | |
| 6,520,980 B1 | 2/2003 | Foerster | |
| 6,524,317 B1 | 2/2003 | Ritchart et al. | |
| 6,527,794 B1 | 3/2003 | McDevitt et al. | |
| 6,527,795 B1 | 3/2003 | Lizardi | |
| 6,533,795 B1 | 3/2003 | Tran et al. | |
| 6,540,770 B1 * | 4/2003 | Tornier et al. | 606/232 |
| 6,544,281 B2 | 4/2003 | ElAttrache et al. | |
| 6,547,800 B2 | 4/2003 | Foerster et al. | |
| 6,551,330 B1 | 4/2003 | Bain et al. | |
| 6,554,852 B1 | 4/2003 | Oberlander | |
| 6,569,187 B1 | 5/2003 | Bonutti et al. | |
| 6,575,987 B1 | 6/2003 | Appell et al. | |
| 6,582,453 B1 | 6/2003 | Tran et al. | |
| 6,585,730 B1 | 7/2003 | Foerster | |
| 6,605,096 B1 | 8/2003 | Ritchart | |
| 6,635,073 B2 | 10/2003 | Bonutti | |
| 6,638,279 B2 | 10/2003 | Bonutti | |
| 6,641,597 B2 | 11/2003 | Burkhart et al. | |
| 6,652,561 B1 | 11/2003 | Tran | |
| 6,656,183 B2 | 12/2003 | Colleran et al. | |
| 6,660,008 B1 | 12/2003 | Foerster et al. | |
| 6,660,023 B2 | 12/2003 | McDevitt et al. | |
| 6,673,094 B1 | 1/2004 | McDevitt et al. | |
| 6,712,830 B2 | 3/2004 | Esplin | |
| 6,770,076 B2 | 8/2004 | Foerster | |
| 6,780,198 B1 | 8/2004 | Gregoire et al. | |
| 6,855,157 B2 | 2/2005 | Foerster et al. | |
| 6,984,241 B2 | 1/2006 | Lubbers et al. | |
| 6,986,781 B2 | 1/2006 | Smith | |
| 7,001,411 B1 | 2/2006 | Dean | |
| 7,041,120 B2 | 5/2006 | Li et al. | |
| 7,056,333 B2 | 6/2006 | Walshe | |
| 7,081,126 B2 | 7/2006 | McDevitt et al. | |
| 7,083,638 B2 | 8/2006 | Foerster | |
| 7,090,690 B2 | 8/2006 | Foerster et al. | |
| 7,144,415 B2 | 12/2006 | Del Rio et al. | |
| 7,153,312 B1 | 12/2006 | Torrie et al. | |
| 7,156,864 B2 | 1/2007 | Lintner | |
| 7,232,455 B2 | 6/2007 | Pedlick et al. | |
| 7,235,100 B2 | 6/2007 | Martinek | |
| 7,247,164 B1 | 7/2007 | Ritchart et al. | |
| 7,329,272 B2 | 2/2008 | Burkhart et al. | |
| 7,491,217 B1 | 2/2009 | Hendren et al. | |
| 7,517,357 B2 | 4/2009 | Abrams et al. | |
| 7,621,950 B1 * | 11/2009 | Globerman et al. | 623/17.11 |
| 7,837,710 B2 | 11/2010 | Lombardo et al. | |
| 8,029,537 B2 | 10/2011 | West, Jr. et al. | |
| 2001/0008971 A1 | 7/2001 | Schwartz et al. | |
| 2001/0018597 A1 | 8/2001 | Gellman et al. | |
| 2001/0051815 A1 | 12/2001 | Esplin | |
| 2001/0051816 A1 | 12/2001 | Enzerink et al. | |
| 2002/0019649 A1 | 2/2002 | Sikora et al. | |
| 2002/0029066 A1 | 3/2002 | Foerster | |
| 2002/0077631 A1 | 6/2002 | Lubbers et al. | |
| 2002/0111653 A1 * | 8/2002 | Foerster | 606/232 |
| 2002/0128684 A1 | 9/2002 | Foerster | |
| 2002/0169478 A1 | 11/2002 | Schwartz et al. | |
| 2002/0188305 A1 | 12/2002 | Foerster et al. | |
| 2003/0018358 A1 | 1/2003 | Saadat | |
| 2003/0088270 A1 | 5/2003 | Lubbers et al. | |
| 2003/0105591 A1 | 6/2003 | Hagiwara | |
| 2003/0144696 A1 | 7/2003 | Sinnott et al. | |
| 2003/0149448 A1 | 8/2003 | Foerster et al. | |
| 2003/0167072 A1 | 9/2003 | Oberlander | |
| 2003/0181925 A1 | 9/2003 | Bain et al. | |
| 2003/0191498 A1 | 10/2003 | Foerster et al. | |
| 2003/0195528 A1 | 10/2003 | Ritchart | |
| 2003/0195563 A1 | 10/2003 | Foerster | |
| 2003/0195564 A1 | 10/2003 | Tran et al. | |
| 2003/0204204 A1 | 10/2003 | Bonutti | |
| 2003/0236555 A1 | 12/2003 | Thornes | |
| 2004/0002735 A1 | 1/2004 | Lizardi et al. | |
| 2004/0024420 A1 | 2/2004 | Lubbers et al. | |
| 2004/0044366 A1 | 3/2004 | Bonutti et al. | |
| 2004/0093031 A1 | 5/2004 | Burkhart et al. | |

| | | | |
|---|---|---|---|
| 2004/0098050 A1 | 5/2004 | Foerster et al. | |
| 2004/0102779 A1 | 5/2004 | Nesper et al. | |
| 2004/0116961 A1 | 6/2004 | Nesper et al. | |
| 2004/0133238 A1 | 7/2004 | Cerier | |
| 2004/0138683 A1 | 7/2004 | Shelton et al. | |
| 2004/0138706 A1 | 7/2004 | Abrams et al. | |
| 2004/0193217 A1 | 9/2004 | Lubbers et al. | |
| 2004/0225325 A1 | 11/2004 | Bonutti | |
| 2004/0243178 A1 | 12/2004 | Haut et al. | |
| 2004/0254609 A1 | 12/2004 | Esplin | |
| 2004/0267317 A1 | 12/2004 | Higgins et al. | |
| 2005/0027307 A1 | 2/2005 | Schwartz et al. | |
| 2005/0055052 A1 | 3/2005 | Lombardo et al. | |
| 2005/0240199 A1 | 10/2005 | Martinek et al. | |
| 2005/0240226 A1 | 10/2005 | Foerster et al. | |
| 2005/0245932 A1 | 11/2005 | Fanton et al. | |
| 2005/0283158 A1 | 12/2005 | West | |
| 2005/0288682 A1 | 12/2005 | Howe | |
| 2006/0067967 A1 | 3/2006 | Bowman et al. | |
| 2006/0079904 A1 | 4/2006 | Thal | |
| 2006/0106423 A1 | 5/2006 | Weisel et al. | |
| 2006/0116719 A1 | 6/2006 | Martinek | |
| 2006/0161159 A1 | 7/2006 | Dreyfuss et al. | |
| 2006/0178702 A1 | 8/2006 | Pierce et al. | |
| 2006/0235413 A1 | 10/2006 | Denham et al. | |
| 2006/0271060 A1 | 11/2006 | Gordon | |
| 2006/0271105 A1 | 11/2006 | Foerster et al. | |
| 2006/0293710 A1 | 12/2006 | Foerster et al. | |
| 2007/0142861 A1 | 6/2007 | Burkhart | |

FOREIGN PATENT DOCUMENTS

| | | | |
|---|---|---|---|
| WO | WO 01/54586 A1 | 8/2001 | |
| WO | WO 01/67962 A2 | 9/2001 | |
| WO | WO 02/11630 A | 2/2002 | |
| WO | WO 02/21998 A2 | 3/2002 | |
| WO | WO 03/065904 A1 | 8/2003 | |
| WO | WO 2004/062506 A1 | 7/2004 | |
| WO | WO 2005/112786 A2 | 12/2005 | |
| WO | WO 2005/112788 A2 | 12/2005 | |
| WO | WO 2006/060035 A2 | 6/2006 | |
| WO | WO 2006/067548 A1 | 6/2006 | |
| WO | WO 2006/128092 A2 | 11/2006 | |
| WO | WO 2007/084714 A2 | 7/2007 | |

OTHER PUBLICATIONS

Mazzocca et al., "Arthroscopic Single-Row Versus Double-Row Suture Anchor Rotator Cuff Repair," *The American Journal of Sports Medicine*, 33:1861 (2005).

Mazzocca et al., Arthroscopic Single versus Double Row Suture Anchor Rotator Cuff Repair, abstract of presentation made on Jun. 25, 2004 at 2004 Annual Meeting of the American Orthopaedic Society for Sports Medicine in Quebec, Canada, publication date unknown.

Millett et al., Mattress double anchor footprint repair: a novel, arthroscopic rotator cuff repair technique, *Arthroscopy: The Journal of Arthroscopic and Related Surgery*, 20(8):875-879 (2004).

Waltrip, Robert L., "A Biomechanical Comparison of Three Techniques," *The American Journal of Sports Medicine*, vol. 31, No. 4, pp. 493-497.

International Search Report and Written Opinion of the International Searching Authority dated Sep. 6, 2006 from PCT/US2005/019454.

International Preliminary Report on Patentability dated Jan. 25, 2007 from PCT/US2005/019454.

PCT, Invitation to Pay Additional Fees, mailed May 13, 2008, for International Application No. PCT/US2007/083662.

Arthrex, Inc., Defendant and Counterclaimant Arthrex, Inc.'s Preliminary Invalidity Contentions (including Appendix 1-4) filed in the United States District Court Southern District of California on Jan. 30, 2012.

Arthrex, Inc., Scope This Out, a Technical Pearls Newsletter for Arthroscopists, 2003, pp. 1-4, vol. 5, No. 3, Arthrex, Inc., USA.

Arthrex, Inc.'s Answer to Plaintiff KFX Medical Corp.'s complaint for Patent Infringement and Counterclaims, United States District Court, Southern District of California, Sep. 23, 2011, Los Angeles, USA.

Arthrex, Inc.'s, Answer to Plaintiff KFX Medical Corp.'s First Amended Complaint for Patent Infringement and Counterclaims, United States District Court, Southern District of California, filed Apr. 23, 2012, Los Angeles, USA.

Arthrex, Inc.'s, Defendant and Counterclaimant Preliminary Invalidity Contentions as to Patent Nos. 8,100,942 and 8,109,969, United States District Court, Southern District of California, filed May 21, 2012.

Arthrex, Inc.'s, Defendant and Counterclaimant Supplemental Preliminary Invalidity Contentions as to U.S. Patent No. 7,585,311, filed May 21, 2012.

Complaint for Patent Infringement, dated Aug. 1, 2011, *KFX Medical Corporation v. Arthrex, Inc.*, (S.D.C.A.).

Lo, et al., Spotlight on Surgical Techniques. Current Concepts in Arthroscopic Rotator Cuff Repair, American Journal of Sports Medicine, 2003, pp. 308-324, vol. 31, No. 2, Sage Publications.

Opus Medical, Inc., the AutoCuff System, Closing the Gap in Soft Tissue Repair, Introducing Totally Arthroscopic Rotator Cuff Repair, Opus Medical, 2003, no page numbers.

Paulos, M.D., Graftjacket Regenerative Tissue Matrix Rotator Cuff, date unknown, Wright Medical Techology, Inc.; Wright Cremascoli Ortho SA.

PCT International Preliminary Report on Patentability, dated May 12, 2009, for International Application No. PCT/US2007/083662.

PCT International Search Report and Written Opinion, dated Aug. 8, 2008, for International Application No. PCT/US2007/083662.

Robbe, M.D. et al., Knotless Suture-based Anchors, Operative Techniques in Sports Medicine, 2004, pp. 221-224, Elsevier Inc.

Seldes, M.D., et al., Tissue Mend Arthroscopic Insertion of a Biologic Rotator Cuff Tissue Augment After Rotator Cuff Repair, Stryker, date unknown, pp. 1-7.

Statement of Tate Scott, dated Apr. 12, 2011, submitted in Re-Examination No. 90/011,430.

TissueMend Advanced Soft Tissue Repair Matrix, Stryker, date unknown.

TissueMend Soft Tissue Repair Matrix, Stryker, 2004, USA.

Yian, M.D., et al., Arthroscopic Repair of SLAP Lesions With a Bioknotless Suture Anchor, Arthroscopy: The Journal of Arthroscopic and Related Surgery, May-Jun. 2004, pp. 547-551, vol. 20, No. 5. Arthroscopy Association of North America.

* cited by examiner

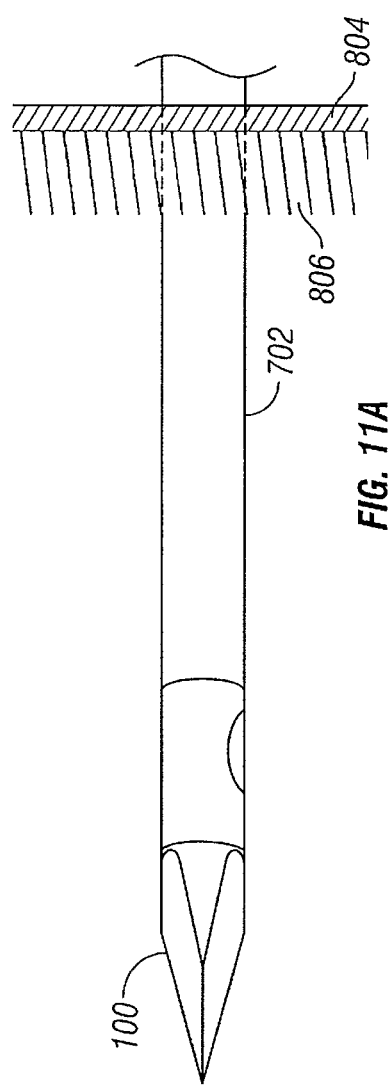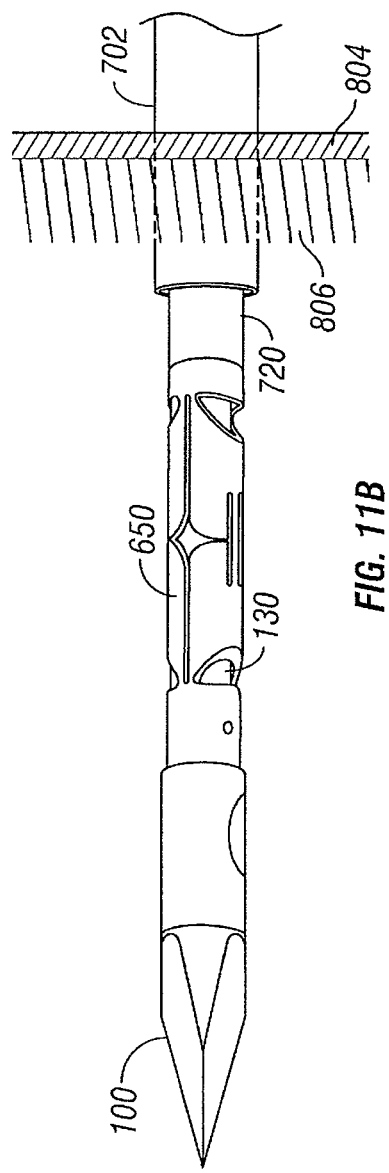

SUTURE ANCHOR

CROSS-REFERENCE TO RELATED APPLICATIONS

This application is a divisional of U.S. application Ser. No. 11/557,027, now U.S. Pat. No. 8,062,334, filed Nov. 6, 2006, which is a continuation-in-part of U.S. application Ser. No. 11/143,007, now U.S. Pat. No. 7,585,311, filed Jun. 1, 2005, which claims the benefit of U.S. Provisional Application Nos. 60/576,477, filed Jun. 2, 2004; 60/610,924, filed Sep. 17, 2004; and 60/634,174, filed Dec. 7, 2004. U.S. application Ser. No. 11/557,027, filed Nov. 6, 2006, also claims the benefit of U.S. Provisional Application No. 60/753,445, filed Dec. 22, 2005. All of these applications are incorporated herein by reference in their entirety.

BACKGROUND OF THE INVENTION

1. Field of the Invention

The present invention relates to medical devices and procedures. More particularly, the present invention relates to suture anchors for insertion into bone.

2. Description of the Related Art

There are several medical procedures where a surgeon needs to have suture material that is secured to bone. For example, the surgeon may desire bone-anchored suture to attach soft tissue such as tendons or other soft connective tissue to the bone. One common example is a torn rotator cuff, where the supraspinatus tendon has separated from the humerus causing pain and loss of ability to elevate and externally rotate the arm. To repair a torn rotator cuff, typically a surgical procedure is used to suture the torn tendon to the bone using a variety of methods. Some procedures utilize large incisions and involve complete detachment of the deltoid muscle from the acromion. Small diameter holes are made in the bone for passing suture material through the bone to secure the tendon. Such large incision procedures are traumatic, causing prolonged pain and recovery time. Other procedures make small incisions and use arthroscopic techniques to attach sutures using either small diameter holes or a bone anchor. However, it is difficult to manipulate sutures within the surgical site using arthroscopic techniques. In addition, when knot tying is used to secure the suture to a bone anchor, it is difficult to properly adjust the tension of the suture while tightening the knot. Accordingly, there is a need for improved anchor systems.

SUMMARY OF THE INVENTION

One embodiment disclosed herein includes a bone anchor that comprises a cylindrical body having cuts formed in its side such that the body can deform under axial force to form one or more lateral features, wherein at least some of the cuts define two convex edges adapted to roll against each other during deformation. In some embodiments, at least some of the cuts define an upper and lower portion of each lateral feature, wherein the upper and lower portions are connected to each other by an uncut portion of the cylindrical body. Some embodiments include a substantially pointed tip positioned on a first end of the cylindrical body. Some embodiments include a suture attached to the tip and extending through the cylindrical body and out a second end of the cylindrical body that is opposite the first end. In some embodiments, the anchor is configured to form two lateral features after deformation. In some embodiments, at least some of the cuts define an upper and lower portion of one of the lateral features and wherein one of the convex edges is an edge of the upper portion of the lateral feature and the other convex edge is an edge of the lower portion of the lateral feature.

Another embodiment disclosed herein includes a method of securing an anchor in bone, the method including inserting the anchor into the bone and deforming the anchor to form one or more lateral features, wherein the deforming comprises causing two convex edges in the anchor to roll against each other as the lateral features are formed. In some embodiments, inserting the anchor into the bone comprises inserting the anchor through soft tissue disposed over the bone. In some embodiments, deforming the anchor comprises applying an axial force to the anchor.

Another embodiment disclosed herein includes a bone anchor, comprising a cylindrical body having cuts formed in its side such that the body can deform under axial force to form one or more lateral features, wherein at least some of the cuts define one or more hinges about which a first portion of the side of the body can bend during deformation and define an edge of the first portion adapted to contact a second portion of the side of the body, wherein the first portion forms part of one of the lateral features after deformation. In some embodiments, the first portion and the second portion are connected to each through the hinges. In some embodiments, the hinges comprise a third portion of the side of the cylindrical body. In some embodiments, the first portion forms a lower portion of one of the lateral features. In some embodiments, the second portion comprises a part of the cylindrical body that is uncut around its circumference. In some embodiments, the second portion comprises a part of the cylindrical body that does not deform under the axial force that forms the one or more lateral features. Some embodiments include a substantially pointed tip positioned on a first end of the cylindrical body. Some embodiments include a suture attached to the tip and extending through the cylindrical body and out a second end of the cylindrical body that is opposite the first end. In some embodiments, the tip is attached to the second portion.

Another embodiment disclosed herein includes a method of securing an anchor in bone, the method including inserting the anchor into the bone and deforming the anchor to form one or more lateral features, wherein the deforming comprises causing an edge of one of the lateral features to contact an undeformed part of the anchor. In some embodiments, inserting the anchor into the bone comprises inserting the anchor through soft tissue disposed over the bone. In some embodiments, deforming the anchor comprises applying an axial force to the anchor.

Another embodiment disclosed herein includes a bone anchor that includes a suture securing portion that comprises a cavity comprising an aperture and a length of wire positioned in the cavity; and a suture secured to the length of wire and extending through the aperture. In some embodiments, the length wire is bent in hook shape. In some embodiments, the length wire is attached to the anchor. In some embodiments, the suture securing portion is part of a substantially pointed anchor tip. In some embodiments, a side of the tip comprises an aperture through which the wire extends. Some embodiments include a weld that secures the wire in the aperture in the side of the tip. In some embodiments, a side of the tip comprises an aperture configured such that a knot in the suture can be inserted therethrough. In some embodiments, the tip is connected to a cylindrical body and the suture extends from the tip through the cylindrical body. In some embodiments, the suture is secured to the length of wire by being tied to the length of wire.

Another embodiment disclosed herein includes a method of securing a suture to a bone anchor, the method including passing the suture through an aperture in the anchor, securing the suture to a length of wire, and positioning the length of wire such that a least a portion of the wire runs generally laterally relative to the axis of the aperture. Some embodiments include securing the wire to the anchor. In some embodiments, securing the wire to the anchor comprises welding the wire to the anchor. In some embodiments, the axis of the aperture is substantially parallel to the axis of the anchor. In some embodiments, passing the suture through the aperture comprises passing the suture through the center of the anchor and out of the aperture. In some embodiments, securing the suture to the length of wire comprises tying the suture to the wire.

Another embodiment disclosed herein includes a bone anchor inserter that includes a handle, an anchor holder coupled to the handle and adapted to be reversibly coupled to a bone anchor, a first tube coupled to the handle and adapted to contact the bone anchor, and an axial movement mechanism disposed within the handle that is adapted to move either the anchor holder or the first tube axially relative to the handle, thereby providing axial force to the bone anchor. In some embodiments, the anchor holder comprises a rod. In some embodiments, the anchor holder comprises a second tube. In some embodiments, the anchor holder is coupled to the handle via screw threads. In some embodiments, the anchor holder is coupled to the handle via a break-away connection adapted to separate from the anchor upon application of a separation force between the anchor holder and the anchor. In some embodiments, the anchor holder is positioned inside of the first tube. In some embodiments, the anchor comprises a substantially pointed tip connected to a cylindrical body and the anchor holder is adapted to be reversibly coupled to the tip. In some embodiments, the anchor comprises a substantially pointed tip connected to a cylindrical body and the first tube is adapted to contact an end of the cylindrical body opposite the tip. Some embodiments include a third tube within which the anchor holder and first tube are positioned. In some embodiments, the anchor comprises a cylindrical body and the third tube is configured to reversibly extend over at least a portion of the cylindrical body. In some embodiments, the axial movement mechanism is configured to also retract the third tube. Some embodiments include a selection mechanism configured to determine whether actuation of the axial movement mechanism provides the axial force to the bone anchor or retracts the third tube. In some embodiments, the axial movement mechanism comprises a ratchet mechanism.

Another embodiment disclosed herein includes method of securing an anchor in bone, the method including inserting the anchor into bone using an anchor inserter comprising a handle, an anchor holder coupled to the handle and the bone anchor, and a first tube and deploying lateral features on the bone anchor by actuating an axial movement mechanism in the handle, the mechanism adapted to move either the anchor holder or the first tube axially relative to the handle, thereby providing axial force to the bone anchor. In some embodiments, inserting the anchor comprises applying an axial force to the handle, thereby providing an axial force to the anchor holder and the anchor. In some embodiments, applying the axial force to the handle comprises hitting the handle with a blunt object. Some embodiments include, after inserting the anchor, retracting a second tube covering at least a portion of the anchor. Some embodiments include, after deploying the lateral features, detaching the anchor holder from the anchor.

BRIEF DESCRIPTION OF THE DRAWINGS

FIG. 11A is a perspective view of a bone anchor coupled to a bone anchor inserter prior to insertion and deployment.

FIG. 11B is a perspective view of a bone anchor coupled to a bone anchor inserter after insertion with a protective outer tube on the inserter retracted.

DETAILED DESCRIPTION OF THE PREFERRED EMBODIMENT

Various embodiments include a bone anchor constructed in such a manner that the bone anchor may have one of two configurations. A first low-profile configuration allows the anchor to be easily inserted into bone. In one embodiment, the bone anchor is inserted into a pre-drilled bone hole. In other embodiments, the bone anchor is inserted directly into bone without pre-drilling. In one embodiment, the bone anchor is inserted by tapping the anchor into the bone. In other embodiments, the bone anchor is inserted by applying a constant axial force to the anchor. In still other embodiments, the bone anchor is inserted by screwing the anchor into the bone. A second configuration of the bone anchor has a larger profile such that the anchor cannot be easily removed from the bone after insertion. In one embodiment, the second configuration is achieved by deploying one or more lateral features that extend laterally away from the axis of the bone anchor. The lateral features prevent the bone anchor from being easily removed from the bone. In one embodiment, the lateral features are deployed by deforming certain portions of the bone anchor.

One embodiment is a bone anchor adapted for piercing through the soft tissue and into underlying bone. In one embodiment, suture material may be pre-attached to the piercing bone anchor so that after implantation, a suture passes from the bone anchor through to the top of the soft tissue for easy passing over the soft tissue.

In one embodiment, the anchor includes a substantially hollow cylinder having a portion of its walls cut in such a manner so as to allow the cylinder to deform under axial stress and form lateral features such as wings. The lateral features prevent the anchor from being easily removed from the bone after deployment. In one embodiment, the anchor comprises a pointed tip coupled to the hollow cylinder for piercing the soft tissue and/or bone. In one embodiment, suture is pre-attached to the pointed tip inside of the hollow cylinder. In other embodiments, suture is pre-attached at other locations on the piercing anchor, such as at the proximal or distal end of the hollow cylinder.

Figure 1A:
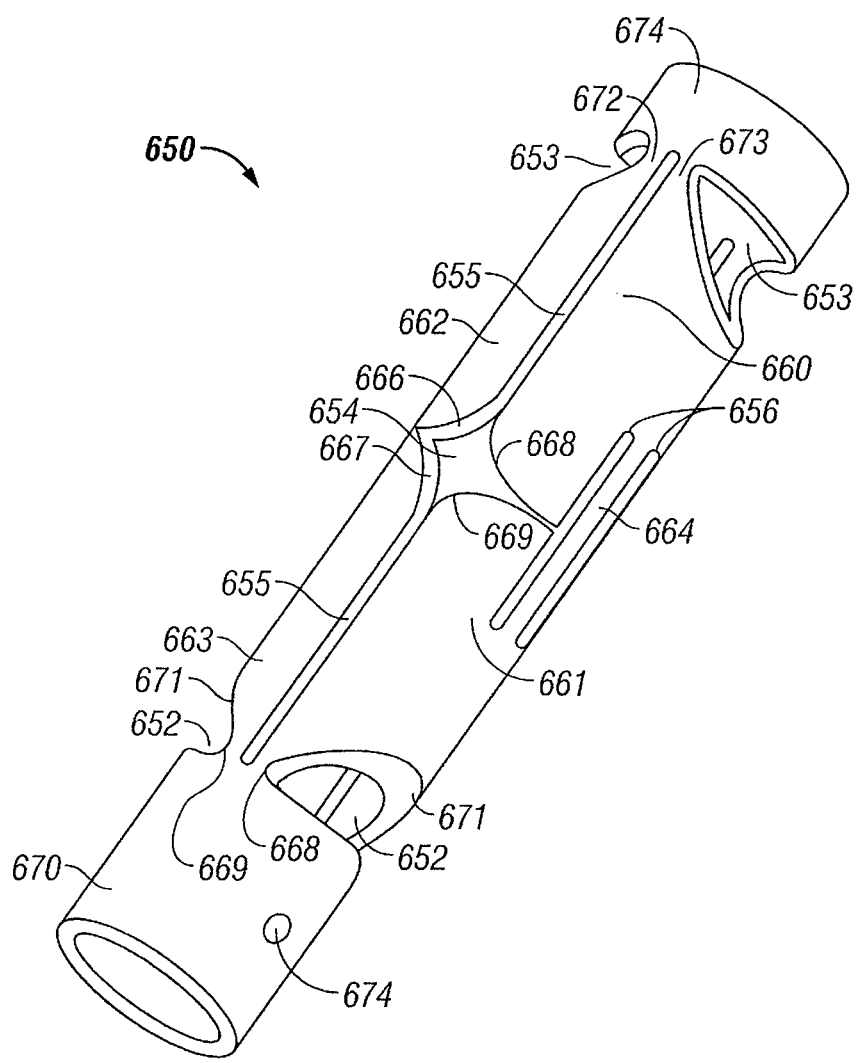
FIG. 1A is a perspective view of a deformable cylinder for use in a bone anchor.
Figure 1B:
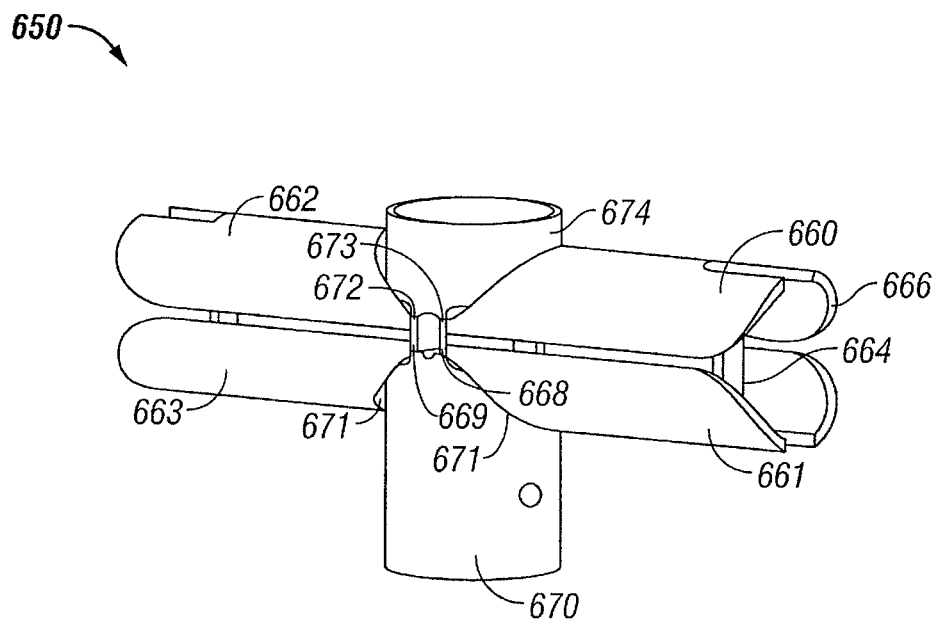
FIG. 1B is a perspective view of the cylinder of FIG. 1A after deformation.

One embodiment of a deformable substantially hollow cylinder is depicted in FIGS. 1A and 1B. In FIG. 1A, the substantially hollow cylinder 650 is depicted in a pre-deployed state. The substantially hollow cylinder 650 has a plurality of cuts 652, 653, 654, 655, and 656 in its side. The cuts 652 form two notches in the cylinder 650 opposite each other near the distal end of the cylinder 650. The cuts 653 form similar notches near the proximal end of the cylinder 650. The cuts 652 define edges 671. The cuts 654 form curved edges 666, 667, 668, and 669. Similar cuts on the opposite side of the cylinder 650 form similar curved edges. Elongated cuts 655 together with cuts 654 (along with their corresponding cuts on the opposite side of the cylinder 650) separate the side of the cylinder into four wall portions 660, 661, 662, and 663. Wall portions 660 and 661 are one side of the cylinder while wall portions 662 and 663 are on the opposite side. Cuts 656 define a rib 664 that connect wall portions 660 and 661 together. Similar cuts on the opposite side of the cylinder 650 define a rib that connects wall portions 662 and 663 together.

Cuts 652 and 655 define hinge portions 668 and 669. Similar hinge portions are defined on the other side of the cylinder 650. The hinge portions 668 and 669 (and corresponding opposite hinge portions) connect the distal wall portions 661 and 663 to a distal uncut wall portion 670 of the cylinder 650. Cuts 655 and 653 define hinge portions 672 and 673. The hinge portions 672 and 673 (and corresponding opposite hinge portions) connect the proximal wall portions 660 and 662 to a proximal uncut wall portion 674 of the cylinder 650. In one embodiment, the distal uncut wall portion 670 includes a weld aperture 674, described in more detail below.

The cuts 652, 653, 654, 655, and 656 in the side of the cylinder 650 may be formed by any suitable cutting tool. In one embodiment, the cutting tool is a precision micromachining tool such as a laser. Those of skill in the art will appreciate that a plurality of cuts may be formed by a single continuous cutting procedure. For example, cuts 654, 655, and part of cuts 656 as depicted in FIG. 1A may be made by a continuous cutting motion that starts at an initiation point and terminates after forming all of the cuts in a continuous loop returning back to the initiation point. Accordingly, by "cuts" it is meant any opening in the side of the cylinder 650 or portion thereof. As discussed above, the cuts define edges in the side of the cylinder 650, which in turn define portions of the cylinder 650 wall.

Upon application of an axial force to the cylinder 650, the cuts allow the cylinder to deform and produce lateral features. Specifically, axial force causes curved edges 668 and 669 to roll against each other such that wall portions 660 and 661 are forced outward in a lateral direction. Similarly, curved edges 666 and 667 roll against each other to force wall portions 662 and 663 laterally outward. The curved edges 666, 667, 668, and 669 ensure that the cylinder 650 deforms in a controlled and consistent manner. The notches formed by cuts 652 and 653 allow wall portions 660, 661, 662, and 663 to bend outward about hinge portions 668, 669, 672, and 673 without interference from the uncut wall portions 670 and 674. Deformation may continue until edges 671 contact the distal uncut wall portion 670.

In FIG. 1B, the cylinder 650 is depicted in the deformed state. Axial force has caused the cylinder 650 to form two lateral wings. One wing contains as an upper portion wall portion 660 and as a lower portion wall portion 661. The other wing contains as an upper portion wall portion 662 and as a lower portion wall portion 663. The lateral wings prevent the anchor from being removed from the bone. Hinge portions 672 and 673 (and corresponding hinge portions on the opposite side of the cylinder 650) connect the upper portions 660 and 662 of the lateral wings to the proximal uncut wall portion 674. Hinge portions 668 and 669 (and corresponding hinge portions on the opposite side of the cylinder 650) connect the lower portions 661 and 663 of the lateral wings to the distal uncut wall portion 670. Rib 664 connects the upper portion 660 with the lower portion 661. A similar rib connects the upper portion 662 with the lower portion 663. The ribs keep all of the portions of the lateral wings in the same plane and increase anchor retention. The edges 671 contact the distal uncut portion 670. This contact substantially increases anchor pull out forces by preventing deformation of the lateral wings when a proximal force is applied to the cylinder 650 after it has been deployed into bone.

In some embodiments, the lateral wings have a "T" shape as depicted in FIG. 1B. In other embodiments, the lateral wings may be angled relative to the axis of the anchor, such as to form a "Y" shape. Such angling may help prevent anchor pull-out from the bone. For example, in one embodiment, the lateral wings angle upward towards the proximal end of the cylinder 650.

Although the cylinder 650 has been described with specific cut patterns, those of skill in the art will appreciate that any number of geometries of cuts in the cylinder 650 may be utilized to create a deformable structure that will produce lateral protrusions upon exposure to stress.

To facilitate insertion of an anchor containing cylinder 650 into bone, a substantially pointed tip may be positioned on the distal end of the cylinder 650. Any suitable shape of tip may be provided. In some embodiments, a conical shaped tip is used. In other embodiments, a pyramidal or other tip having flat angled sides is provided. In some embodiments, the tip includes features to facilitate attachment of a suture to the tip. For example, the tip may include a suture eyelet or suture knot receiving aperture. In such embodiments, suture may be secured to the tip and then extend through the hollow cylinder 650 out of the open proximal end of the cylinder 650.

Figure 2:
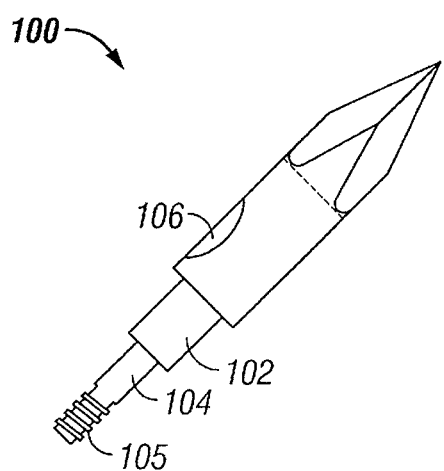
FIG. 2 is a perspective view of an anchor tip for use in a bone anchor.

FIG. 2 depicts one embodiment of a tip 100 that may be positioned on the distal end of the cylinder 650. The tip includes cylinder coupling portion 102 adapted to fit inside of the distal uncut wall portion 670 of cylinder 650. The cylinder coupling portion 102 may be secured to the cylinder 650 by welding through weld aperture 674 in the side of the distal uncut wall portion 670 of cylinder 650. The tip 100 further includes an anchor holder coupling mechanism 104 that will extend into the interior of the hollow cylinder 650. The anchor holder coupling mechanism 104 is configured such that it can be reversibly coupled to an anchor holder that is part of an anchor inserter. The anchor holder may thus extend into the hollow cylinder 650 through the opening on the proximal end of the cylinder 650 and then couple to the anchor holder coupling mechanism 104. This design permits the driving force of inserting the anchor into bone to be applied directly to the tip 100, thereby avoiding axial force being applied to the cylinder 650 during anchor insertion and potential premature deployment. In addition, the coupling of the anchor tip 100 to the anchor holder provides an attachment point near the distal end of the cylinder 650 to aid in providing axial force to the cylinder 650 during deployment. In one embodiment, the anchor holder coupling mechanism 104 includes threads 105 as depicted in FIG. 2 such that the anchor holder may be screwed onto the anchor holder coupling mechanism 104. Those of skill in the art will appreciate other mechanisms that may be used to couple the tip 100 to an anchor holder. In some embodiments, a break-away attachment is formed, such as a weak weld that will break upon application of a separation force between the anchor tip 100 and the anchor holder. Tip 100 also includes a suture knot aperture 106 for securing a suture to the tip as described in more detail below.

Figure 3:
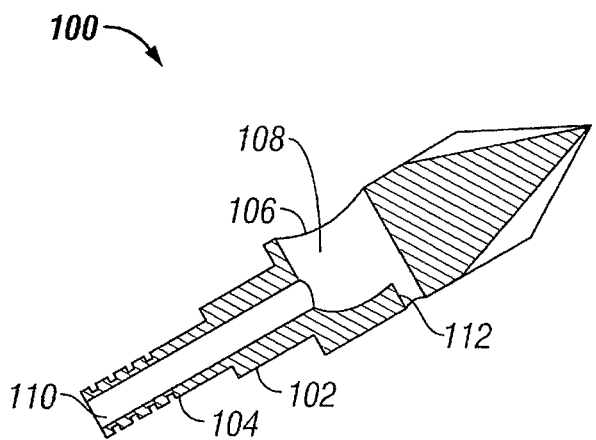
FIG. 3 is a cross-sectional view of the anchor tip of FIG. 2.

FIG. 3 depicts a cross-sectional view of anchor tip 100. As noted above, the tip 100 includes a suture knot aperture 106. The aperture 106 leads into a suture knot cavity 108 in which a suture knot may be placed. The cavity 108 is also in communication with a shaft 110 that extends through the cylinder coupling portion 102 and anchor holder coupling mechanism 104 through which suture material may pass. In some embodiments, suture is secured to the tip 100 by first passing the suture through the shaft 110 and out of aperture 106. A knot may be tied in the suture which can then be seated in cavity 108. The size of the knot prevents the suture from being pulled back through the shaft 110. In some embodiments, a feature may be included within the cavity 108 to which the suture may be tied or otherwise secured to further increase suture pull-out forces. In some embodiments, the feature may have a portion that extends generally laterally within the cavity 108 such that it cannot be pulled into the shaft 110. For example, a piece of wire to which the suture may be tied can be inserted into the cavity 108. In some embodiments, the wire may be bent into a shape such as a hook shape to prevent the suture knot from sliding off of the wire. In some embodiments, the feature may include a ring (e.g., a split ring) to which the suture will be secured or looped through. An aperture 112 may be provided in which the lateral feature (e.g., wire) may be secured.

Figure 4A:
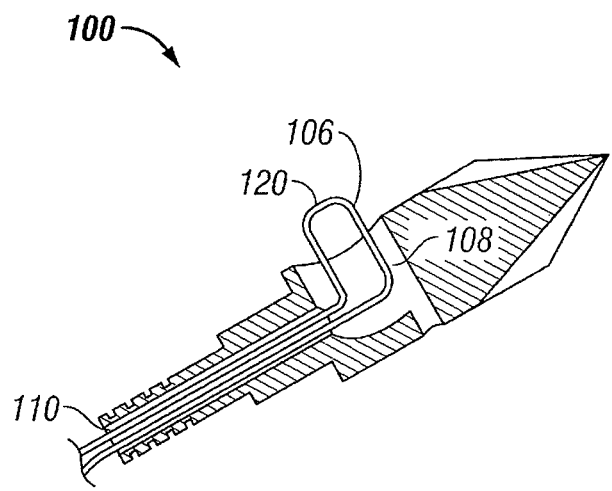
FIG. 4A is a cross-sectional view of the anchor tip of FIGS. 2 and 3 with suture material passed therethrough.
Figure 4B:
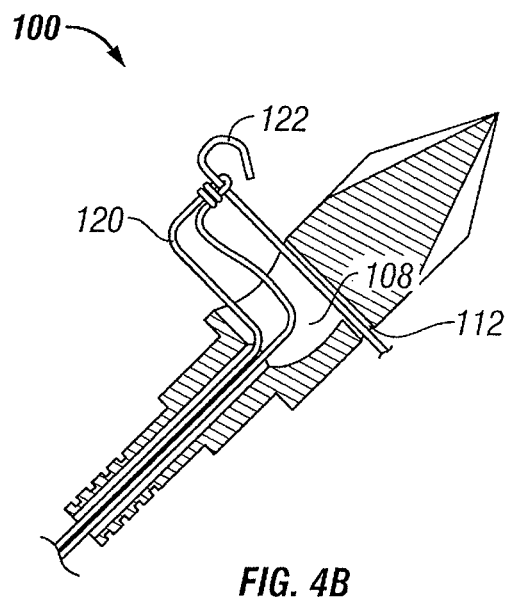
FIG. 4B is a cross-sectional view of the anchor tip of FIGS. 2 and 3 with a wire passed therethrough and suture material tied to the wire.
Figure 4C:
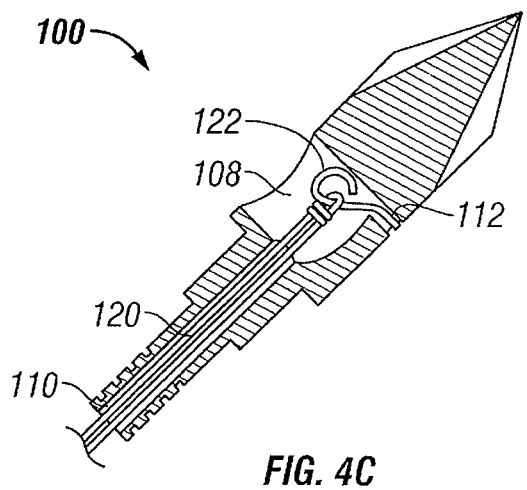
FIG. 4C is a cross-sectional view of the anchor tip of FIGS. 2 and 3 with a wire with attached suture positioned inside of the tip.

FIGS. 4A-4C depict cross-sectional views of one method of securing a suture to the tip 100. In FIG. 4A, a length of suture 120 is pulled through the shaft 110 into the cavity 108 and out of the suture knot aperture 106. As depicted in FIG. 4A, the suture 120 may be doubled over such that two lengths of the suture 120 extend through the shaft 110 and a loop is pulled through the aperture 106. In other embodiments, only a single length of suture is pulled through the shaft 110. In still other embodiments, two separate lengths of suture are pulled through the shaft 110 such that two suture ends are pulled out of aperture 106. The suture loop depicted in FIG. 4A may be pulled through the shaft 110 using a length of wire that is bent inside of the loop; however, any suitable method of pulling the suture through the shaft 110 may be used.

As depicted in FIG. 4B, the suture 120 is next tied about a piece of wire 122. In some embodiments, as depicted in FIG. 4B, the wire 122 may be shaped into a hook so that the suture knot does not easily slide off of the wire 122. The straight end of the wire 122 is inserted into the aperture 112 and the hook portion and suture knot are pulled into the cavity 108. Once the suture knot and wire hook are seated within the cavity 108, the straight portion of the wire extending through the aperture 112 may be trimmed and the wire welded to the tip 100 at the aperture 112 as depicted in FIG. 4C. The welded wire 112 provides a generally laterally running portion that prevents the wire 112, and hence the suture 120, from being pulled into the shaft 110. While a wire hook has been described, it will be appreciated that any suitable feature may be employed within cavity 108 to prevent the suture from being pulled out of the cavity 108. For example, any other generally laterally running feature may be utilized. In general, the suture may be secured to any feature having a size in at least one dimension that is larger than the diameter of the shaft 110. Other suitable shapes include block or spherical structures.

While specific structures have been described for attaching a suture to the tip 100, it will be appreciated that any suitable structures and methods for attaching suture may be used, including but not limited to tying the suture to an eyelet, clamping the suture between a portion of the tip 100 and the inside of the cylinder 650, adhering the suture to the tip 100 by welding or use of an adhesive, or any other suitable means.

Figure 5A:
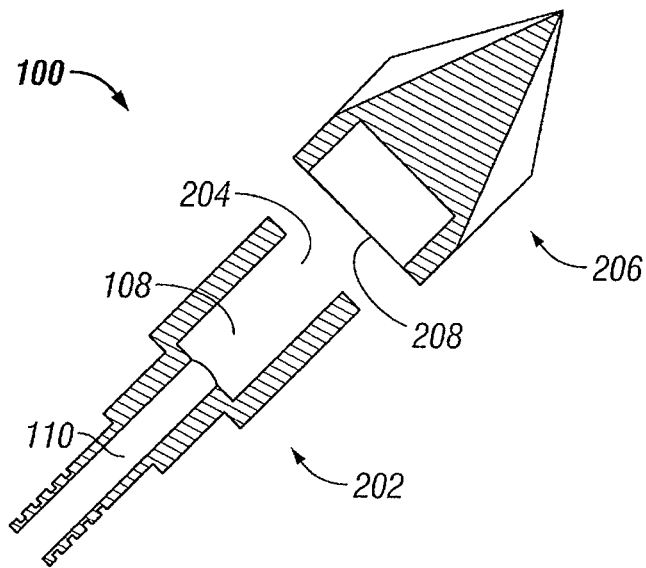
FIG. 5A is a cross-sectional view of a two-piece anchor tip.

In one alternative embodiment, depicted in FIGS. 5A-5D, the anchor tip 100 may comprise a two-part structure. As depicted in FIG. 5A, a proximal portion 202 includes a shaft 110 as in the embodiment of FIGS. 4A-4C and a suture knot cavity 108 in communication with the shaft 110. Instead of apertures in the side of the anchor tip 100, the end of proximal portion 202 contains an aperture 204 in communication with the suture knot cavity 108. A separate distal portion 206 of the anchor tip 100 comprises an aperture 208 for receiving the proximal portion 202.

Figure 5B:
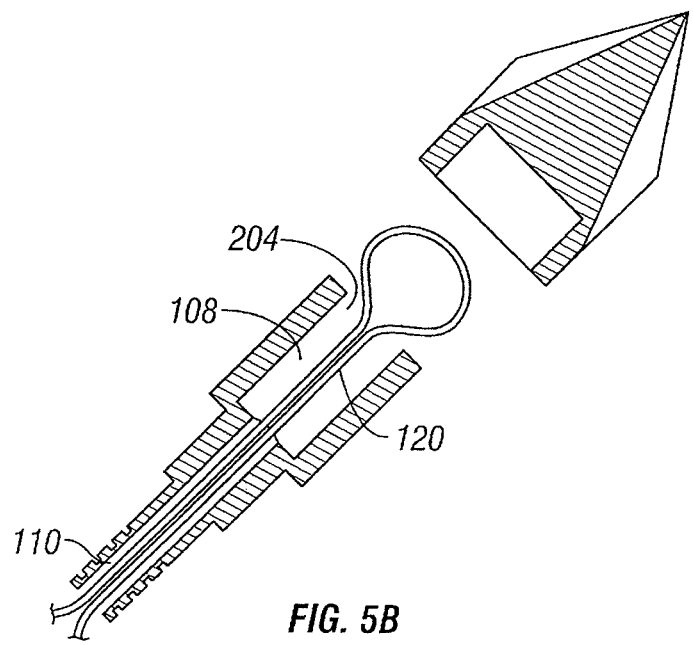
FIG. 5B is a cross-sectional view of the two-piece anchor tip of FIG. 5A with suture material passed through one piece.
Figure 5C:
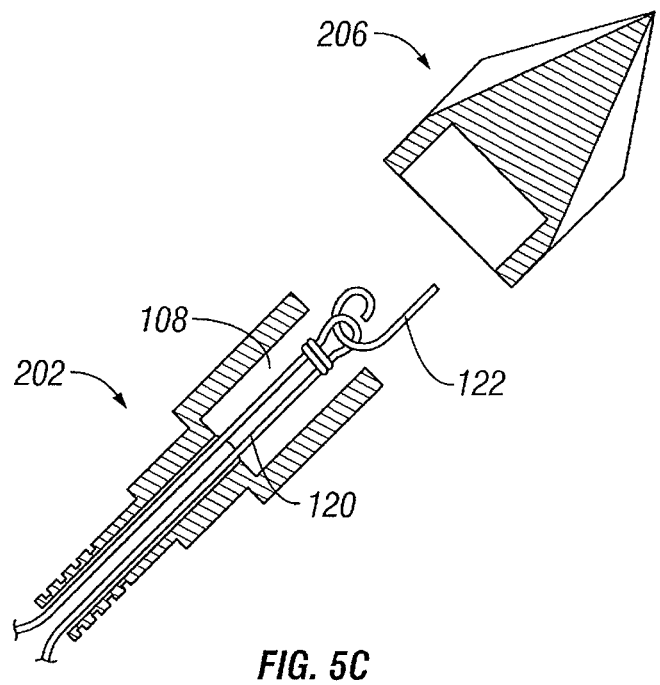
FIG. 5C is a cross-sectional view of the two-piece anchor tip of FIG. 5A with suture material tied to a wire.
Figure 5D:
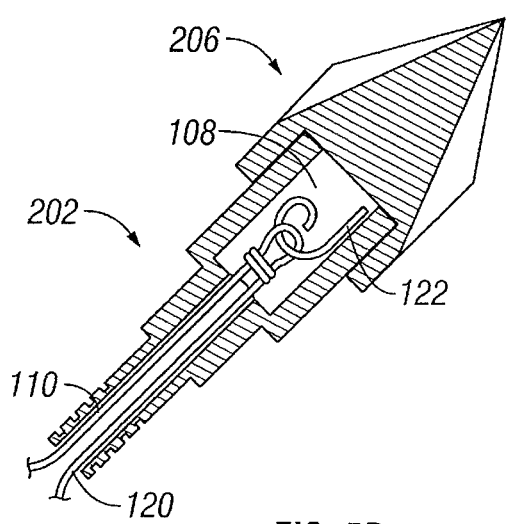
FIG. 5D is a cross-sectional view of the two-piece anchor tip of FIG. 5A with both pieces coupled together.

To secure a suture 120 to the anchor tip 100, the suture 120 may be pulled through the shaft 110 into the cavity 108 and out of the aperture 204 (see FIG. 5B). The suture 120 may then be formed into a knot or optionally tied around a structure such as wire hook 122 much in the same way as described above for FIGS. 4A-4C (see FIG. 5C). The hook 122 may be seated in the cavity 108 to prevent the suture 120 from being pulled through the shaft 110 (see FIG. 5D). The distal portion 206 of the anchor tip 100 may then be coupled to the proximal portion 202 by inserting the proximal portion 202 into the aperture 208 in the distal portion 206. The proximal potion 202 and distal portions 206 may be secured together through a force fit, friction fit, screw threading, welding (e.g., laser welding), adhesive, or any other suitable means.

In one alternative of the above embodiment, the distal portion 206 has the same diameter as the proximal portion 202. In this alternative, the proximal portion 202 is not completely inserted into the aperture 208 of the distal portion 206. Instead, the aperture 208 is aligned with the cavity 208 and then the distal portion 206 and the proximal portion 202 are welded together. In some embodiments, the contacting edges between the distal portion 206 and proximal portion 202 are tapered to improve lateral stability and alignment of the parts.

Those of skill in the art will also appreciate that in this embodiment, the volume of the suture knot cavity 108 may be entirely within the proximal portion 202, entirely within the distal portion 208, or divided between the proximal portion 202 and the distal portion 208.

Figure 6:
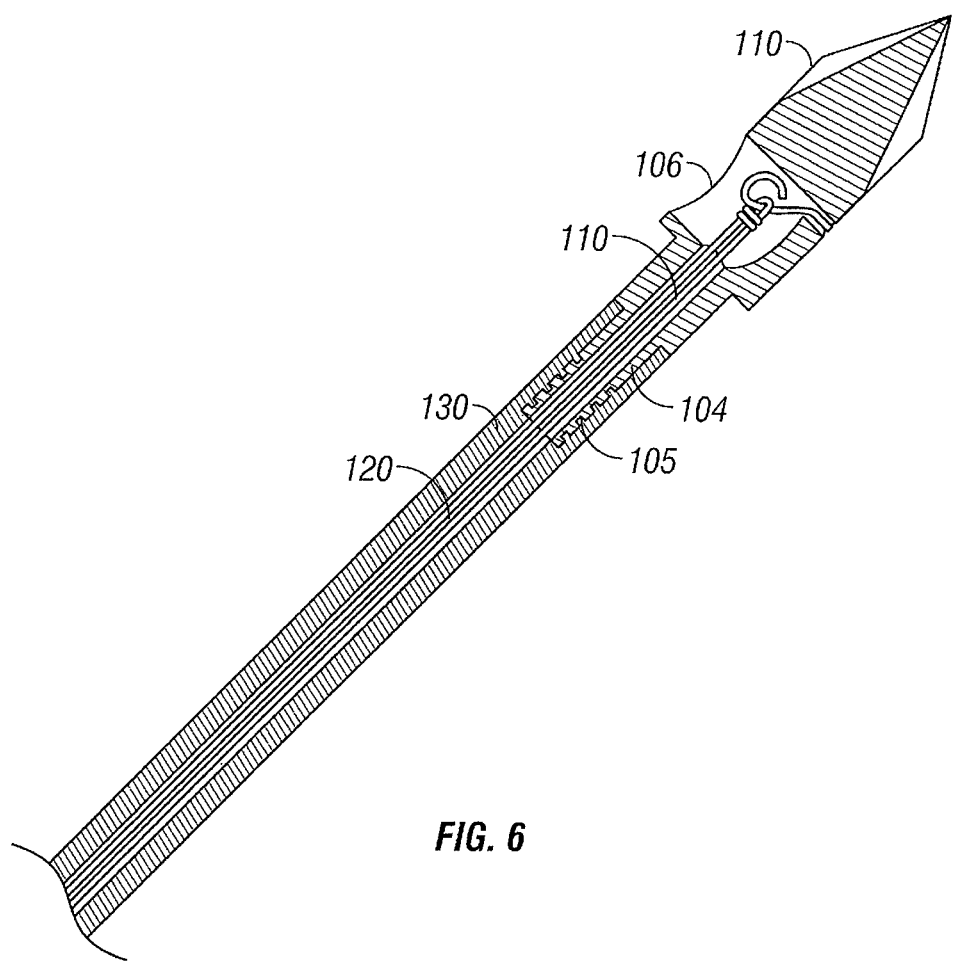
FIG. 6 is a cross-sectional view of a bone anchor tip coupled to an anchor holder.

Either before or after the suture 120 is attached to the anchor tip 100, an anchor holder may be coupled to the tip 100 via anchor holder coupling mechanism 104. For example, as depicted in cross-section in FIG. 6, an anchor holder 130, may be attached to the anchor holder coupling mechanism 104 by screwing the holder 130 onto the threads 105 of the anchor holder coupling mechanism 104. In some embodiments, the anchor holder 130 is a hollow tube such that the suture 120 may extend through shaft 110 and through the hollow center of the anchor holder 130. The suture 120 may be threaded through the anchor holder 130 either before or after the suture 120 is secured to the tip 110. In one embodiment, the loop formed by the suture 120 (see FIG. 4A) is pulled through the anchor holder 130 tube and then through the shaft 110 and out of the aperture 106. In an alternative embodiment, the anchor holder 130 is a non-hollow rod. In such an embodiment, the suture 120 may extend through an aperture in the tip and/or suture holder 130 such that suture can run along the outside of the suture holder 130.

Either before or after the suture holder 130 is coupled to the tip 100 and either before or after the suture 120 is attached to the anchor tip 100, the cylinder 650 as described above may be attached to the suture tip 100. As depicted in cross-section in FIG. 7, the cylinder 650 may be slid over the cylinder coupling portion 102 of the tip 100. The cylinder 650 may then be secured to the tip 100 by welding inside of the weld aperture 674 in the side of the cylinder 650; however, any suitable attachment mechanism may be utilized such as a forced fit, frictional fit, threads, adhesive, or any other suitable means. The structure depicted in FIG. 7 allows the proximal portion of the cylinder 650 to freely move relative to the anchor holder 130 during deformation. In addition, the anchor holder 130 can be freely attached or de-attached from the tip 100 at the anchor holder coupling mechanism 104 inside of the cylinder 650. Thus, after anchor insertion and deployment, the anchor holder 130 may be de-attached from the tip 100 and removed, leaving the suture 120 extending from the tip 100 and through the deformed cylinder 650.

In some embodiments, the anchor tip 100 may include a shoulder, barbs, or other suitable structures for preventing the anchor from sliding out of soft tissue through which it is pierced. Such structures enable the soft tissue to be pierced and then moved using the anchor prior to inserting the anchor into underlying bone. For example, in repairing a torn rotator cuff, it may be desirable to use the anchor to reposition the tendon to the desired location prior to inserting the anchor into bone. Those of skill in the art will appreciate other structures that may be used to facilitate engagement with soft tissue so that it can be manipulated.

Figure 8:
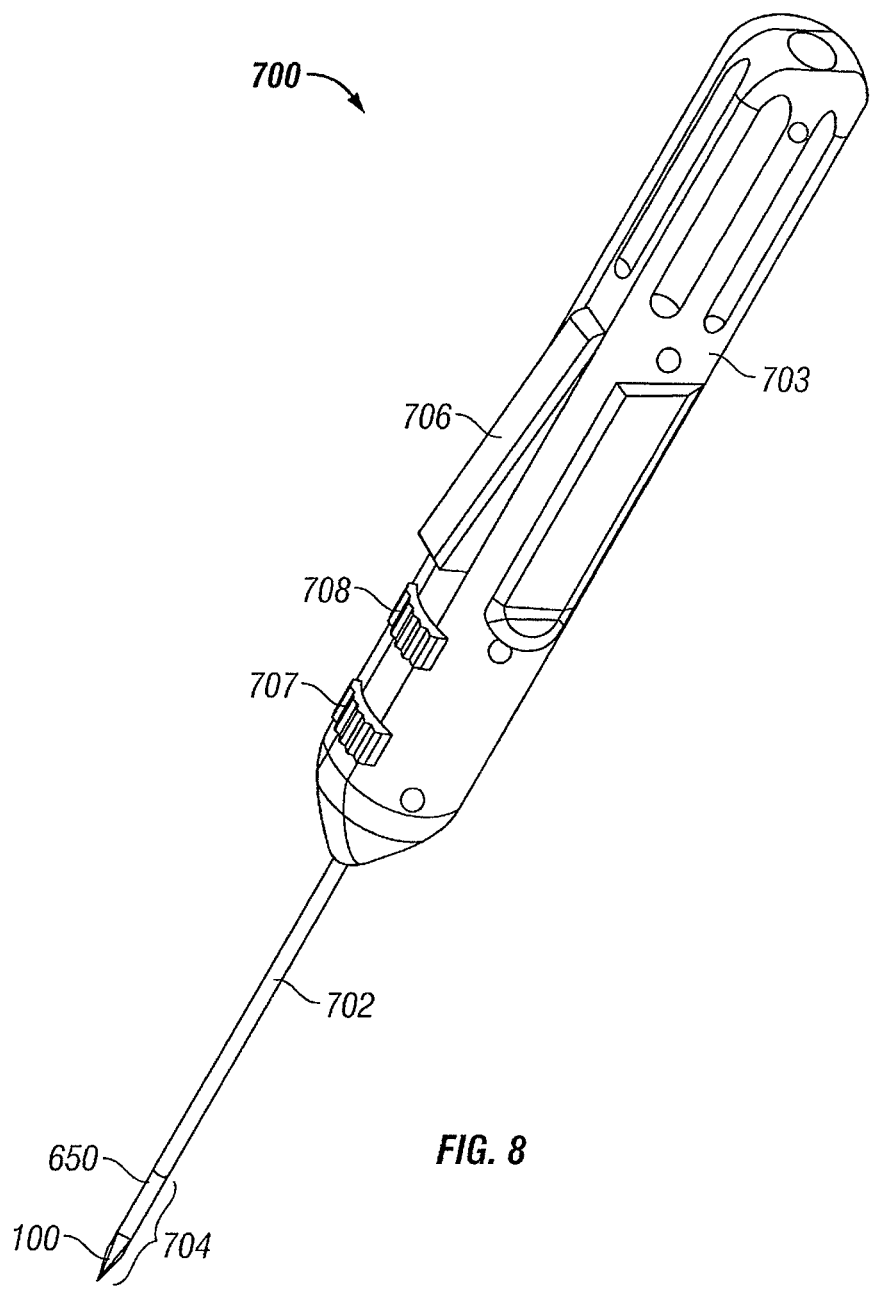
FIG. 8 is a perspective view of a bone anchor inserter.

One embodiment of an inserter device 700 that may be used to insert and deploy the anchors 704 described herein is depicted in FIG. 8. The inserter 700 includes a handle 703 configured for easy handling and manipulation by a surgeon. The handle 703 may include one or more control features configured to allow the surgeon to actuate the deployment of the anchor 704 and any other feature of the inserter 700. For example, as depicted in FIG. 8, the handle 703 may include two release buttons, outer tube release button 707 and deployment release button 708. In addition, the handle includes a deployment lever 706 which may be used to drive the actuation of various features of the inserter 700, as described below. For example, if the outer tube release button 707 is pressed, pressing one or more times on the deployment lever 706 may cause an outer tube 702 on the inserter to retract, thereby exposing the deformable cylinder 650. If the deployment release button 708 is pressed, pressing one or more times on the deployment lever 706 may cause an axial force to be applied to the deformable cylinder 650 to deform it as described above. The buttons 707 and 708 may be interlocked such that button 708 cannot be pressed and activated until button 707 has been pressed and the outer tube 702 retracted. After the outer tube 702 has been retracted, pressing button 708 can lock tube 702 in place and simultaneously detaching a pawl, thereby allowing the ratchet system to be dedicated to deforming cylinder 650.

Figure 7:
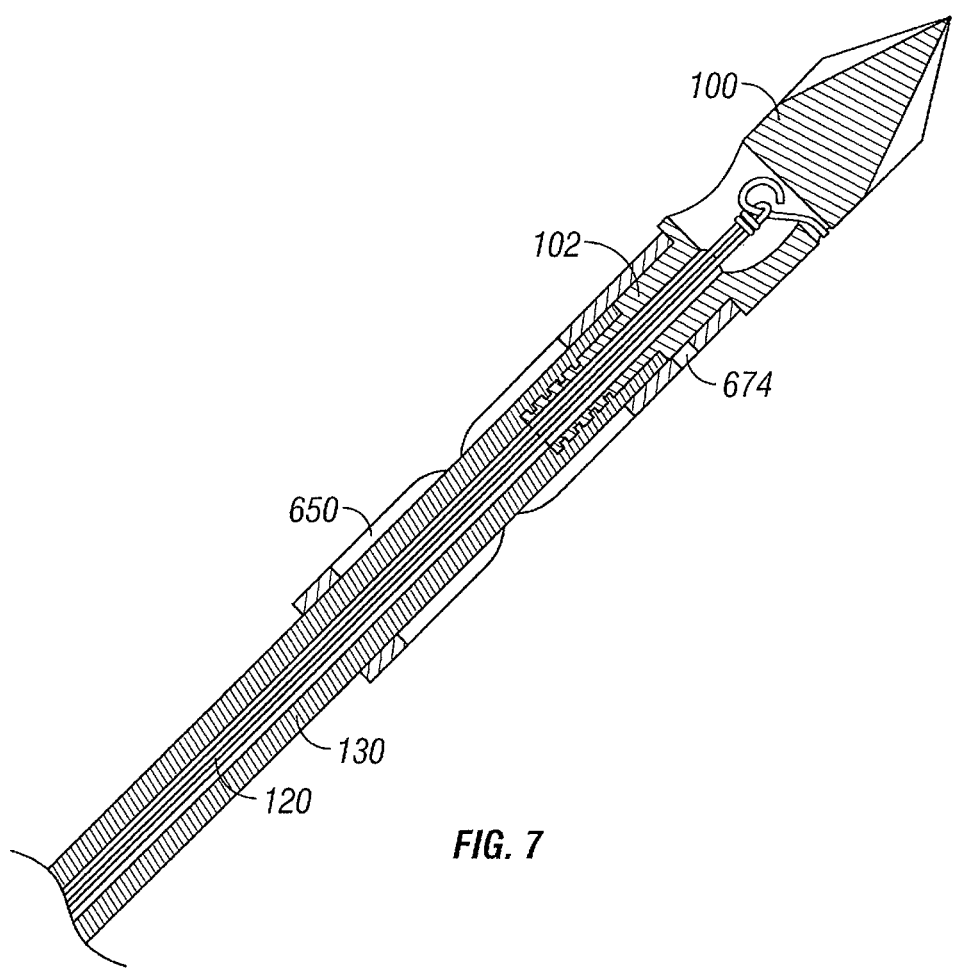
FIG. 7 is a cross-sectional view of the bone anchor tip and anchor holder of FIG. 6 with the deformable cylinder of FIG. 1A attached thereto.
Figure 9:
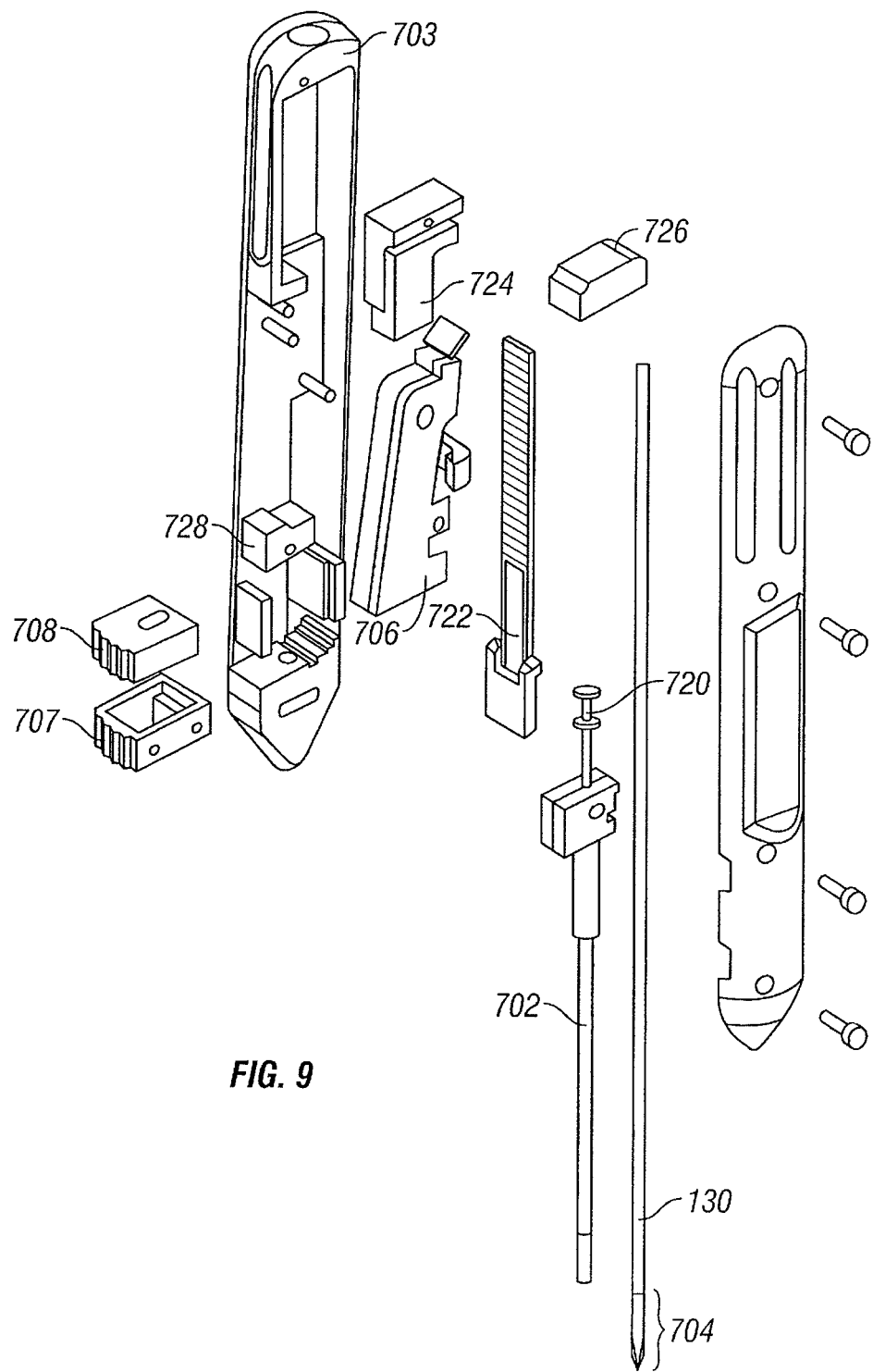
FIG. 9 is an exploded view of the bone anchor inserter of FIG. 8.
Figure 10:
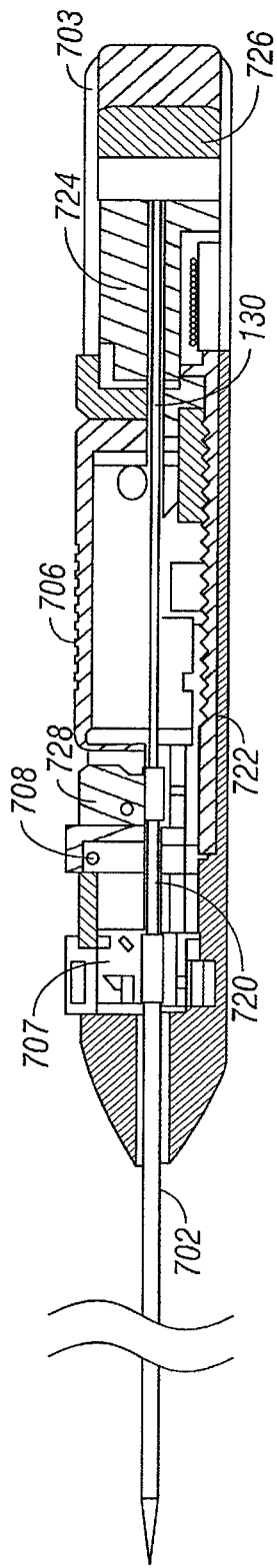
FIG. 10 is a cross-sectional view of the bone anchor inserter of FIGS. 8 and 9.

FIG. 9 depicts an exploded view of the inserter device 700 and FIG. 10 depicts a cross-sectional view. These figures illustrate that three concentric tubes extend from the inserter handle 703 to the anchor 704. The anchor holder tube 130, discussed above, extends inside of the anchor 704 where it reversibly couples to the anchor tip 100 as depicted in FIG. 7. When the anchor inserter 700 is fully assembled, the anchor holder tube 130 extends through the inside of an anchor push tube 720. The anchor push tube 720 in turn extends through the inside of the outer tube 702. The anchor push tube 720 contacts the top part of the deformable cylinder 650 such that when the anchor push tube 720 and the anchor holder tube 130 are moved relative to each other, the cylinder 650 is compressed, thereby deploying the anchor as discussed above. The outer tube 702 may extend over the cylinder 650 during insertion of the anchor to help prevent premature deployment. After insertion, the outer tube 702 may be retracted prior to initiating relative movement between the anchor holder tube 130 and the anchor push tube 720.

The anchor holder tube 130 is secured to a draw block 724 that is disposed in the proximal part of the handle 703. The draw block 724 can move axially in the handle until in contacts a stop block 726, thereby moving the anchor holder tube 130 axially. The anchor push tube 720 is fixedly secured to the handle at block 728. The outer tube 702 terminates in the region of outer tube release button 707. When outer tube release button 707 is in a first position, the outer tube 702 can be moved axially. When outer tube release button 702 is in a second position, the outer tube 702 is fixed relative to the handle 703.

The deployment lever 706 engages a rack assembly 722 such that compression of the deployment lever 706 causes a ratchet mechanism on the deployment lever 706 to move the rack assembly 722 inside the handle 703. Thus, repeated compression of the deployment lever 706 causes the rack assembly 722 to move axially through the handle 703. As mentioned above, the anchor inserter 700 includes an outer tube release button 707 and a deployment release button 708. When the outer tube release button 707 is pressed, compression of the deployment lever 706 and concomitant movement of the rack assembly 622 pulls the outer tube 702 further into the handle 703, thereby retracting the outer tube 702 from the anchor 704. When the deployment release button 708 is pressed, compression of the deployment lever 706 and concomitant movement of the rack assembly 622 pushes the draw block 724 in a proximal direction, thereby pulling the anchor holder tube 130 further into the handle 703. Because the anchor push tube 720 is fixed relative to the handle 703, the proximal movement of the anchor holder tube 130 causes an axial force to be applied to the cylinder 650, thereby deforming it as described above.

Although one particular inserter system has been described, it will be appreciated that many other inserter systems are also suitable for inserting the anchor 704 and deploying the cylinder 650. For example, while the above-described system causes the anchor holder tube 130 to move relative to the handle 703 while anchor push tube 720 is kept stationary, other embodiments may cause the anchor push tube 720 to move while keeping the anchor holder tube 130 stationary. In addition, some embodiments may include mechanisms for moving both anchor holder tube 130 and anchor push tube 720 in order to apply axial compression to the cylinder 650. In other embodiments, a rod instead of a tube may be used for anchor holder tube 130. In still other embodiments, a wire may be used.

In an alternative embodiment, mechanisms may be employed such that a surgeon does not have to use significant manual force to deploy the anchor. For example, a shape-memory material such as nitinol or an electric motor may be employed to effect deployment.

In some embodiments, visual indicators may be provided in the inserter handle 700 to provide feedback to a surgeon, such as indicating the deployment state of the anchor or the depth of anchor insertion.

Those of skill in the art will appreciate other mechanisms that could be used for deploying a deployable anchor and providing safety mechanisms to prevent premature deployment.

Figure 11C:
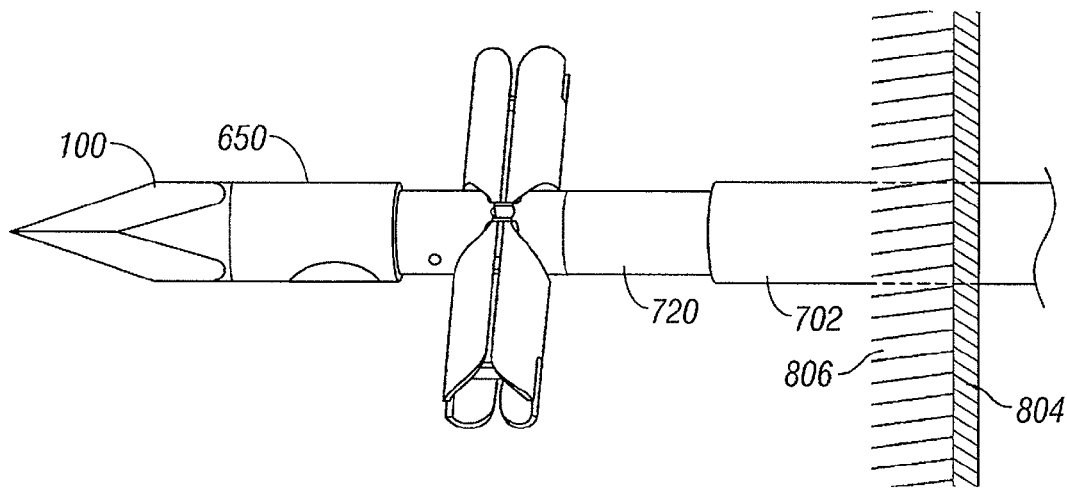
FIG. 11C is a perspective view of a bone anchor coupled to a bone anchor inserter after deployment of the anchor.

FIGS. 11A-11D illustrate deployment of the anchor described above using the above-described inserter. FIG. 11A depicts the anchor-inserter configuration during insertion. Outer tube 702 covers the deformable cylinder 650 to prevent deployment during insertion. The anchor tip 100 is exposed for piercing of bone 806 and intervening tissue 804. The anchor may be driven by tapping on the proximal end of the handle of the anchor inserter. The axial force is transmitted through the anchor holder tube 130 directly to the anchor tip 100 such that it is forced into the bone 806. Thus, during insertion, minimal axial stress is supplied to the deformable cylinder 650.

As depicted in FIG. 11B, after anchor insertion, the outer tube 702 is retracted to expose the deformable cylinder 650. FIG. 11B also depicts the anchor push tube 720 contacting the proximal end of the deformable cylinder 650 and the anchor holder tube 130 coupled to the anchor tip. Next, axial force is applied to the deformable cylinder 650 by inducing relative movement between the anchor holder tube 130 and the anchor push tube 720, such as by retracting the anchor holder tube 130 further into the inserter handle as described above. FIG. 11C depicts the resulting deployment of lateral wings on the cylinder 650 within the bone 806.

Figure 11D:
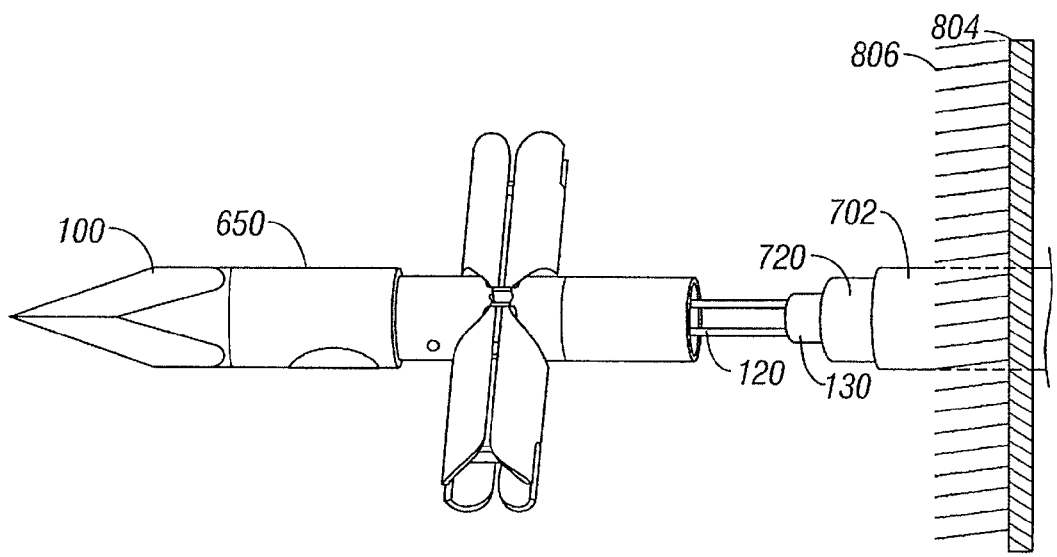
FIG. 11D is a perspective view of a bone anchor after separation from a bone anchor inserter.

Finally, after deployment the anchor inserter is decoupled from the anchor by detaching the anchor holder tube 130 from the anchor tip 100. In some embodiments, the anchor holder tube 130 is coupled to the anchor tip 100 via threads on the anchor holder tube 130 and the anchor tip 100. In such embodiments, decoupling is achieved by rotating the inserter handle to unscrew the anchor holder tube 130 from the anchor tip 100. In other embodiments, decoupling is achieved by providing a separation force between the anchor holder tube 130 and the anchor tip 100 such that a weak portion of the coupling breaks. For example, in one embodiment, the anchor holder tube 130 is connected to the anchor tip 100 through a weak weld or scored portion of the anchor holder tube 130 that can break when forces in excess of the deployment force is applied. In one embodiment, continued actuation of the deployment actuation mechanism (e.g., ratchet mechanism) after deployment of the anchor supplies enough axial force that the anchor holder tube 130 breaks free from the anchor. FIG. 11D depicts the anchor inserter, along with anchor holder tube 130, anchor push tube 720, and outer tube 702 being retracted from the anchor and removed from the bone 806 and soft tissue 804. As described above, one or more suture lengths 120 may be attached to the anchor tip 100. During anchor insertion and deployment, these suture lengths 120 may be disposed within anchor holder tube 130. Upon decoupling of the anchor holder tube 120 from the anchor tip 100, the anchor inserter may be removed from the insertion site causing the suture lengths 120 to pull out of the anchor holder tube 120 and remain attached to the deployed anchor, ready for further use. In some embodiments, the suture lengths 120 terminate at free ends in the anchor holder tube 120 such that removal of the anchor inserter leaves free suture ends extending from the anchor. In other embodiments, the sutures may remain coupled to the anchor inserter, such is on a suture reel, and are cut to the desired length at a desired time.

In some embodiments, the inserter may have one or more markings to aid a surgeon in inserting the anchor to the proper depth. For example, the inserter may have markings on the outer tube 702 that indicate the depth of the anchor relative to the outer surface of the skin (i.e., the surgeon would look at the inserter markings outside of the patient). Other markings on the outer tube 702 could be used to indicate the depth of the anchor relative to the top surface of soft tissue that is being pierced. A surgeon can use these markings to make sure that the anchor is inserted to the proper depth to insure proper deployment as well as prevent over-insertion. In still other embodiments, markings on the outer tube 702 are used to indicate the depth of the anchor relative to the top surface of the bone that the anchor is being inserted into.

The anchor described herein may be used for any use where a surgeon requires one or more lengths of suture secured to bone. Various embodiments include methods for attaching soft tissue to bone or coupling bone to bone. In one embodiment, a bone anchor described above is inserted through soft tissue into underlying bone and then one or more lengths of suture that are pre-attached to the anchor are passed over the soft tissue and secured to another bone anchor.

Figure 12A:
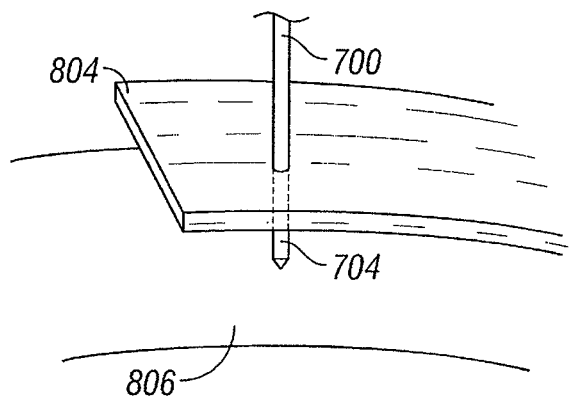
FIG. 12A is a perspective view of a bone anchor and bone anchor inserter pierced through soft tissue.
Figure 12B:
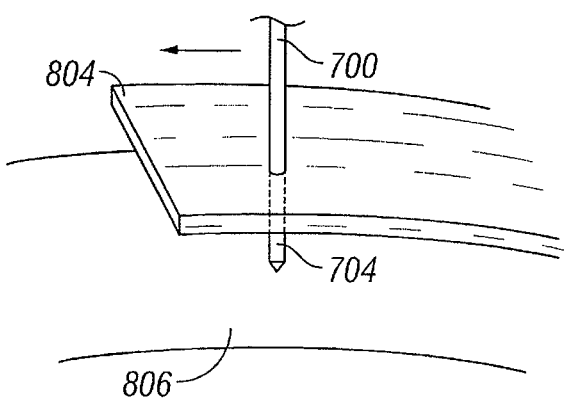
FIG. 12B is a perspective view of a bone anchor and bone anchor inserter stretching soft tissue.
Figure 12C:
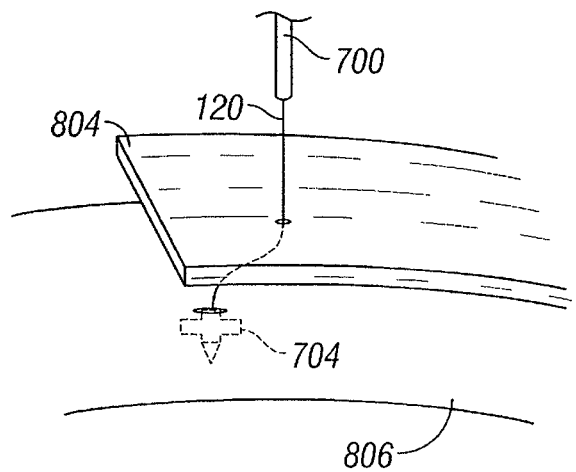
FIG. 12C is a perspective view of a bone anchor and bone anchor inserter after anchor deployment.

One example of such a procedure is depicted in FIGS. 12A through 12F. In FIG. 12A, the anchor 704 described herein (attached to the anchor inserter 700) is pierced through soft tissue 804 that has become detached from underlying bone 806. In FIG. 12B, the anchor inserter 700 is moved laterally relative to the bone 806 so as to stretch the soft tissue 804 laterally relative to the bone 806. As discussed above, structures such as barbs or shoulders may be employed on piercing anchor 704 to facilitate manipulation of the soft tissue 804. In an alternative embodiment, a tissue grasper, such as described in U.S. Provisional Application No. 60/812,836, filed Jun. 12, 2006, which is incorporated herein by reference in its entirety, may be used to stretch the soft tissue 804 to the desired location. Once the soft tissue 804 has been stretched to the desired position, the anchor 704 is inserted into the bone 806 and the anchor 704 is deployed as described above. The inserter 700 is then detached from the anchor 704, leaving a suture 120 attached to the anchor 704 and extending through the soft tissue 804. The anchor 704 may be inserted into bone 806 by tapping on the inserter 700 with a hammer or by any other suitable means of applying axial force. FIG. 12C depicts the deployed anchor 704 with attached suture 120 being pulled out of the inserter 700.

Figure 12D:
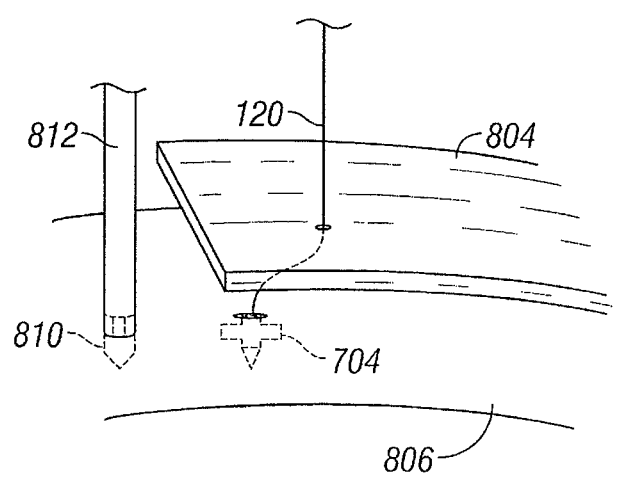
FIG. 12D is a perspective view showing insertion of a second bone anchor after the insertion depicted in FIGS. 12A-12C.
Figure 12E:
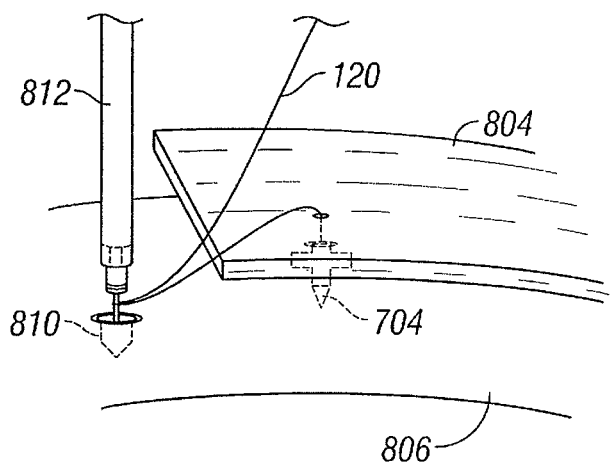
FIG. 12E is a perspective view showing capture of a suture in the second bone anchor depicted in FIG. 12D.

In some embodiments, after insertion of the anchor 704, a suture capturing anchor 810, such as that described in U.S. Application Publication No. 2006-0004364, filed Jun. 1, 2005, which is incorporated herein by reference in its entirety, is inserted into the bone 806 using an inserter 812, as depicted in FIG. 12D. In FIG. 12E, the inserter 812 may be of a type that is then retracted to expose a suture capturing mechanism.

Figure 12F:
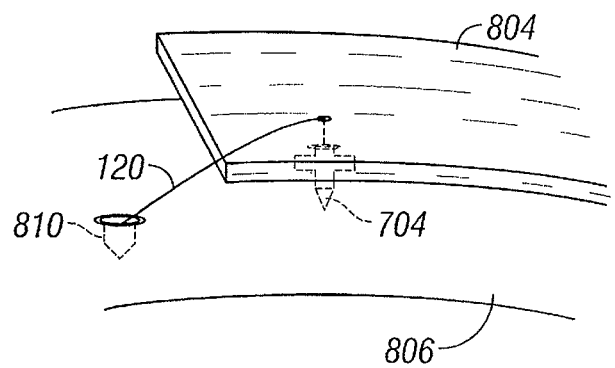
FIG. 12F is a perspective view showing soft tissue secured by a suture extending between two bone anchors.

The suture 120 may then passed over the soft tissue 804 and moved into the suture capturing mechanism and tensioned. Finally, as depicted in FIG. 12F, the suture capturing mechanism may be deployed to capture the suture 120, the anchor inserter 812 detached from the anchor 810, and the suture 120 cut flush with the anchor 810. The result is a length of suture 120 between the bone anchors 704 and 810 that presses the soft tissue 804 against the bone 806. Multiple anchors and sutures may be used to produce any variety of geometries, such as described in U.S. Application Publication No. 2006-0004364, filed Jun. 1, 2005, which is incorporated herein by reference in its entirety.

It will be appreciated that there are numerous stitches, suture threading patterns, and anchor patterns that may be used to secure soft tissue to bone by the methods and devices described herein. These variations as well as variations in the design of the above described anchor devices and inserter devices are within the scope of the present disclosure. In one alternative embodiment, multiple anchors 704 described above may be inserted through soft tissue into underlying bone and suture material run between each of the anchors. For example, in one embodiment, an anchor employing the deformable cylinder 650 described above may be provided that has a suture securing mechanism that can secure suture that is not pre-attached. After insertion of a first anchor with a pre-attached suture through soft tissue, the suture may be attached to additional anchors that have a suture securing mechanism that are also inserted through the soft tissue. Thus, multiple anchors under the soft tissue may be employed with suture extending between them holding the soft tissue against the bone. In some embodiments, the suture may be coupled to the anchors prior to insertion and then fixedly secured after insertion and tensioning. In other embodiments, the suture may be attached to the anchors after insertion.

Although the invention has been described with reference to embodiments and examples, it should be understood that numerous and various modifications can be made without departing from the spirit of the invention. Accordingly, the invention is limited only by the following claims.

What is claimed is:

1. A method of securing an anchor in bone, the method comprising:
    inserting the anchor into the bone; and
    deforming the anchor to form one or more lateral features, wherein said deforming comprises causing two convex edges in the anchor to roll against each other as the lateral features are formed.

2. The method of claim 1, wherein inserting the anchor into the bone comprises inserting the anchor through soft tissue disposed over the bone.

3. The method of claim 1, wherein deforming the anchor comprises applying an axial force to the anchor.

4. The method of claim 1, wherein said deforming comprises causing an edge of one of the lateral features to contact an undeformed part of the anchor.

5. A method of securing a suture to a bone anchor, the method comprises:
    passing the suture through an aperture in the anchor;
    securing the suture to a length of wire;
    positioning the length of wire such that a least a portion of the wire guns generally laterally relative to the axis of the aperture; and
    deforming the anchor to form one or more lateral features, wherein said deforming comprises causing two convex edges in the anchor to roll against each other as the lateral features are formed.

6. The method of claim 5, comprising securing the wire to the anchor.

7. A method of claim 6, wherein securing the wire to the anchor comprises welding the wire to the anchor.

8. The method of claim 5, wherein the axis of the aperture is substantially parallel to the axis of the anchor.

9. The method of claim 8, wherein passing the suture through the aperture comprises passing the suture through the center of the anchor and out of the aperture.

10. The method of claim 5, wherein securing the suture to the length of wire comprises tying the suture to the wire.

11. A method of securing an anchor in bone, the method comprising:
    inserting the anchor into bone using an anchor inserter comprising a handle, an anchor holder coupled to the handle and the bone anchor, and a first tube; and
    deploying lateral features on the bone anchor by actuating an axial movement mechanism in the handle, the mechanism adapted to move either the anchor holder or the first tube axially relative to the handle, thereby providing axial force to the bone anchor,
    wherein said deploying lateral features comprises causing two convex edges in the anchor to roll against each other as the lateral features are formed.

12. The method of claim 11, wherein inserting the anchor comprises applying an axial force to the handle, thereby providing an axial force to the anchor holder and the anchor.

13. The method of claim 12, wherein applying the axial force to the handle comprises hitting the handle with a blunt object.

14. The method of claim 11, comprising, after inserting the anchor, retracting a second tube covering at least a portion of the anchor.

15. The method of claim 11, comprising, after deploying the lateral features, detaching the anchor holder from the anchor.

* * * * *